United States Patent [19]
Goldman

[11] Patent Number: 5,923,398
[45] Date of Patent: *Jul. 13, 1999

[54] INTERACTIVE LIGHT FIELD FOR NON-VISUAL STIMULATION

[75] Inventor: Neil Goldman, Burke, Va.

[73] Assignee: Enlightened Technologies, Inc., Fairfax, Va.

[*] Notice: This patent is subject to a terminal disclaimer.

[21] Appl. No.: 09/033,669

[22] Filed: Mar. 3, 1998

Related U.S. Application Data

[63] Continuation-in-part of application No. 08/662,539, Jun. 13, 1996, Pat. No. 5,805,267
[60] Provisional application No. 60/000,685, Jun. 15, 1995.

[51] Int. Cl.[6] .................................................... A61B 3/10
[52] U.S. Cl. ................................... 351/203; 351/200
[58] Field of Search ................................ 351/203, 200, 351/41, 158, 44

[56] References Cited

U.S. PATENT DOCUMENTS

| | | | |
|---|---|---|---|
| 5,060,062 | 10/1991 | Dotson | 351/201 |
| 5,805,267 | 9/1998 | Goldman | 351/203 |

OTHER PUBLICATIONS

"Adler's Physiology of the Eye"; F.H. Adler; publ. C.B. Mosby, St. Louis, MO; 1975 (Chapter 23).
"Adler's Physiology of the Eye"; F.H. Adler; publ. C.B. Mosby, St. Louis, MO; (pp. 525, 647–673).
"Light Treatment for Circadian and Sleep Disturbances of Shift Work"; C.I. Eastman; Bulletin SOC for Light Treat. & Bio. Rhy.;6; No. 4; Jun. 1994.

"Mechanisms in the Eye that Mediate the Biological and Therapeutic Effects"; G. Brainard, et al.; Proceedings of Light and Biological Rhythms of Man; publ. Pergamon Press, 1993.

"Photoreceptors regulating Circadian Behavior: A Mouse Model"; R.G. Foster, et al.; J. Biol. Rhy. 8; S17–S23, 1993.

"Clinical Opthamology"; T. Duane; vol. 2; Publ. Harper & Row, New York, NY; 1981; (Chapter 2).

"A Comparison of Pulmonary Artery, Rectal and Tympanic Membrane Temperature Measurement in the ICU"; D.G. Klein et al.; Heart Lung, Sep.–Oct. 1993; 22 (5); 435–441.

*Primary Examiner*—Hung Xuan Dang

[57] ABSTRACT

Off axis photon stimulation of a person's eye, provided by a light field which is either uniform or interactive depending on pupil position, provides for biological and/or psychological benefits. The photon stimulation is advantageously provided using eye wear with embedded or affixed light delivery elements such as fiber optic members.

5 Claims, 3 Drawing Sheets

INTERACTIVE LIGHT FIELD FOR NON-VISUAL STIMULATION

CROSS-REFERENCE TO RELATED APPLICATIONS

This patent application is a continuation-in-part (CIP) application of the prior patent application filed Jun. 13, 1996, having U.S. Ser. No. 08/662,539, now U.S. Pat. No. 5,805,267, which itself is a CIP application of the provisional patent application filed Jun. 15, 1995, having U.S. Ser. No. 60/000,685, and the complete contents of both applications are herein incorporated by reference.

DESCRIPTION

BACKGROUND OF THE INVENTION

1. Field of the Invention

The present invention pertains to off-axis light stimulation delivered to a person's pupils for inducing biological responses in the person without impairing vision.

2. Description of the Prior Art

One of the most fundamental characteristics of life on the earth is the way all living things change to adjust to the twenty four hour variations in the physical environment. Indeed, the majority of all biochemical, physiological and behavioral variables in humans fluctuates on a rhythmic basis with a period of about twenty four hours. It is now well established that these daily rhythms are temporally organized by a twenty four hour (i.e., circadian) clock which, in mammals, is located in the suprachlasmatic nucleus (SCN) of the hypothalamus. The circadian system maintains temporal synchronization between the organism and the external environment, as well as the optimal internal coordination of diverse physiological processes in time. The light-dark cycle is the primary environmental agent that synchronizes the endogenous clock, whose intrinsic period is almost always slightly different than twenty four hours (e.g. twenty three-twenty five hours), to the changes in the physical environment that occur within a period of twenty four hours, due to the rotation of the earth on its axis. The ability of the natural light-dark (LD) cycle to entrain circadian rhythms is based on the response of the circadian pacemaker to light. Thus, light pulses presented during early subjective night induce phase delays of the circadian clock, while light exposure during the late subjective night produces phase advances. In mammals, a special tract of nerves, referred to as the retinohypothalmic tract (RHT), carry information about the light-dark environment directly from the retina to the SCN.

Under normal conditions, there is a stable phase relationship among circadian rhythmicity, sleep, and the light-dark cycle. In animals living under natural conditions, uncoupling of sleep and circadian rhythmicity from their normal phase, relative to the entraining light-dark cycle rarely, if ever, occurs. However, humans routinely disrupt the normal synchronization of the sleep-wake and light-dark cycles, either for short periods of time (i.e., following rapid travel across time zones, referred to as the "jet lag" syndrome), or for long periods of time (i.e., as occurs in "shift-workers"). Furthermore, humans are also able to ignore signals from the circadian clock system indicating that it is time to sleep, and can also override the homeostatic need for sleep as occurs during prolonged periods of wakefulness. A number of acute and chronic adverse effects of both shift-work and jet-lag on human health, safety, performance and productivity have now been well documented.

SUMMARY OF THE INVENTION

It is an object of the present invention to provide eye wear which can adjust or maintain a circadian rhythm despite natural light influences.

It is yet another object of the invention to produce a light field in eye wear to be worn close to the pupil which will provide photo stimulation off fovea in the retinal region while still maintaining a sight level of visual acuity to the surrounding physical environment.

It is still another object of the invention to produce an interactive light field emanating from eye wear which produces off axis photo stimulation at the back of the wearer's eye (retinal region).

According to the invention, eye wear in the form of glasses, goggles, clip-on lenses and clip-on rings or other elements is provided which directs light energy from fiber optic elements or optical wave guides into a wearer's eye at an angle that is off-axis from the periphery of the pupil. The wearer's photoreceptors in the retinal region off the fovia will be stimulated (e.g., photoreceptors in the blood vessels, receptors in the cells in front of the rods and cones, and any other receptors in this region); however, the wearer's visual acuity will not be impaired since the main image or "external environmental scene" will be perpendicular to the pupil and will be readily discerned by the wearer.

In one form of the invention, ring shaped illumination elements are positioned in front of the wearer's eyes and project light energy uniformly inward. The optimum arrangement would be circular-like (e.g., circular, eliptical, stretched or compressed circle, etc.) in form with the closest light directing members located just inside the outer edge of the iris, thus enabling the delivery of light in the complete 360° of the off-fovia region. Preferably, the circular-like ring elements will have an inner diameter of 1–3 cm, and most preferably approximately 2 cm. The center of the array corresponds to the center of the pupil in the forward gaze, and preferably does not contain elements so as to allow unimpaired visual accuity. The ring shaped illumination elements can be incorporated into the lenses of glasses or goggles, or can be provided as clip-on elements to be attached to the wearer's glasses, or can simply be free standing light rings without lenses, placed 9–17 mm. in front of the eye. If the ring shaped elements are incorporated into lenses, the angle of the light delivery elements (e.g., fiber optics) and their positions will need to be modified to accommodate the curvature of the lens. In addition, to allow for some lateral movement of the eye without encountering a fiber end, the ring shaped elements can be "stretched" or otherwise enlarged to an elliptical form. Light can be uniformly provided to the wearer to influence "alertness" as well as other biological parameters (e.g., experiments have shown that uniform off-axis illumination can suppress plasma melatonin levels in human subjects). Uniform off-axis illumination will tend to cause the pupil to move towards a position aligned with the center of the ring shaped illumination elements in response to bright light emitted from the light delivery elements. This, in turn, will further assure uniform angular distribution of the illumination around the retina and off the fovea since the pupil will be centrally positioned. Variable spectra and intensity models for illumination can be applied to the light sources so as to permit the simulation of sunrise and sunset with a faithful representation of the associated spectrum at each point in this lighting cycle. Furthermore, the variable spectra and intensity control mode may be used for other applications such as for psychological or seratonergic stimuli and other photo neurological stimuli.

In another embodiment, the eye-wear, such as eye glasses or goggles, are provided with either lenses having embedded therein a fiber optic mesh or lenses having a series of optical wave guides in a thin dielectric medium formed in or on a surface of the lenses. In either case in this second embodiment, the objective is to produce an interactive light field (ILF) at the back of the wearer's eye (retinal region). In order for the subject to see clearly through the glasses or goggles, controlled light enters from the periphery of the pupil, at an angle, such that the main image (i.e., the external environment scene) enters perpendicular to the pupil. Prism-like structures or reflective coatings can be positioned at the ends of the fibers or wave guides to extract the light into the eyes. The fiber mesh or series of wave guides which are used to deliver the ILF can also be used to track the pupil of the wearer. The fibers in the fiber mesh or the wave guides are preferably approximately index matched to the lens medium, such that they are essentially transparent to the wearer. The fibers or wave guides can act as both transmitters and receivers in order to control the illumination process. For example, some of the fibers or wave guides can face outward in order to sense the ambient external environment while others face inward to adjust the illumination to the rear of the eye. Sleep warning alarm systems can also be included to alert the wearer should the eyes exhibit slow rolling movement or the pupils fixate or the eyes stay closed too long. The ILF may allow for measuring other parameters in the eye to make the unit more interactive. The mesh density, light intensities, frequencies, wave forms, and lighting patterns are selectively combined to minimize the photon flux and maintain biological response while maintaining visual acuity. Additionally, light pulses can be temporally, spatially, and spectrally adjusted to reach these goals. Dose rate and dose, both in terms of intensity and photon flux, may be controlled. In a very bright close to the center matrix configuration, the lower half of the lens could be selectively controlled by setting with a dimmer to reduce a potential glare effect with certain users. The necessary hardware electronics preferably fit in the arm of the glasses between the ears and the face.

BRIEF DESCRIPTION OF THE DRAWINGS

The foregoing and other objects, aspects and advantages will be better understood from the following detailed description of the preferred embodiments of the invention with reference to the, drawings, in which.

DETAILED DESCRIPTION OF THE PREFERRED EMBODIMENTS OF THE INVENTION

Figure 1:
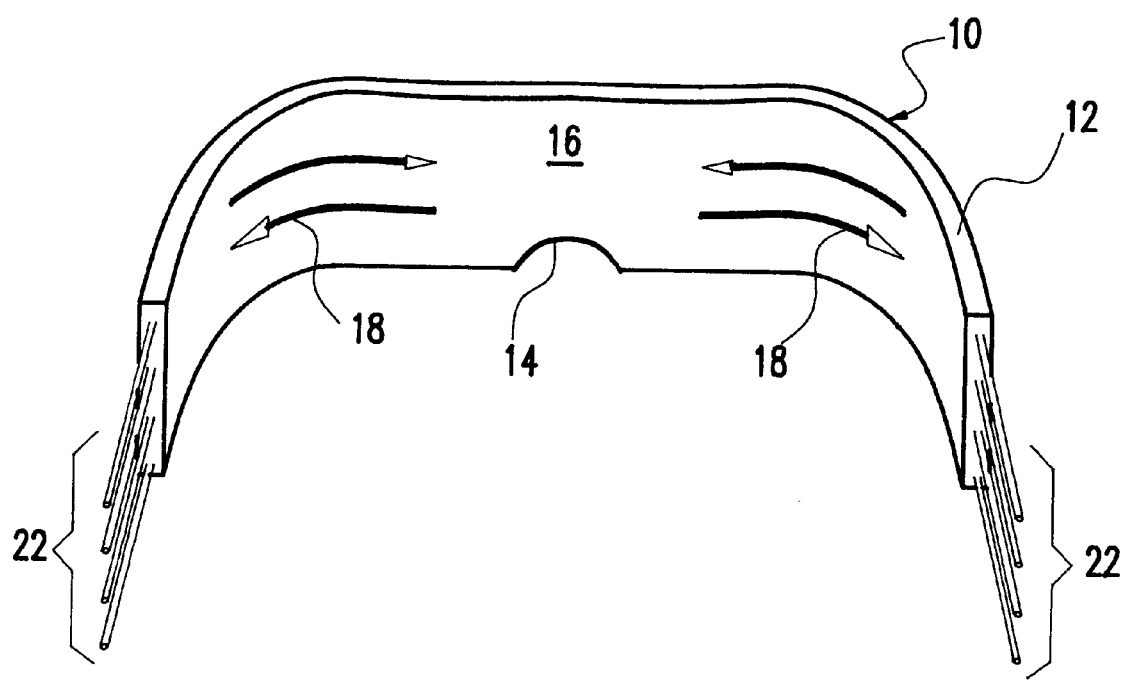
FIG. 1 is a rear perspective view of the front piece of the interactive light field device of the present invention.

The present invention delivers general illumination to the back of the eye in order to provoke a biological response; for example, to influence the wearer's circadian rhythm. In order for the subject to see the surrounding world clearly, light is introduced from the periphery of the pupil such that the outside scene will enter "normal" or "perpendicular" to the pupil, as with ordinary eye-glasses.

The Stiles-Crawford effect of the first kind dictates that light rays from an object point entering the pupil perpendicularly are more effective at stimulating vision than light rays entering the periphery of the pupil. This appears to be related to the fact that peripheral rays entering the cone's inner segments obliquely are not transmitted to the outer segments as efficiently as are rays parallel to the cones axis. Thus, this invention takes advantage of the Stiles-Crawford effect of the first kind with respect to permitting the subject to clearly see his surrounding environment.

The invention also takes advantage of the Stiles-Crawford effect of the second kind wherein peripheral rays entering the cone's inner segments obliquely produce a color sensation somewhat different than that produced by axial rays. This effect or interactions with the nearby ganglia stimulates the biological signals to the suprachiasmatic nucleus, or internal biological clock.

Some of the applications of this invention may require as much as three to six hours of exposure. Experimental results with human subjects have shown that extended exposure to off-axis light stimulation with broad spectrum white light results in melatonin suppression. Preferably, light emitting diodes (LEDs) or other monochromatic light sources can be used in the eye wear since recent human and animal experiments indicate that green light is as effective as broad sun-like spectrum illumination for stimulating a biological response. Miniature metal halide arc light sources may also be used and have the advantage of being transportable, and cool running. In addition, in many applications control of the light wavelengths and light intensity delivered to the eye is desired; thus, control circuitry, optical components, and light field controlling methods may be provided to selectively deliver light of a desired intensity and wavelengths.

The present invention is preferably accomplished with the necessary electronics comfortably fitting in the eye-wear arm between the ears and the front face of the eye-wear using LEDs and fiber optic and/or optical wave guide couplers. However, the off-axis illumination can be provided by clip-on ring or clip-on lens elements which fit onto a wearer's eyeglasses, and by other means. In addition, in laboratory and clinical applications, it may be advantageous to have ring illumination members without lenses which are positioned in front of a person's eyes (e.g., optician's trial frames).

One of the goals of this invention is to illuminate only part of the surface of the eye so that energy isn't lost illuminating the outside portion of the eye. Illumination can be uniformly distributed off fovea in the retinal region, or be selectively provided by an ILF. In either case, the light field provided to the wearer's eye is preferably at an acute angle, or off-axis, with respect to his or her pupil. That is, with uniform illuminating ring elements, the light delivery members (e.g., fiber optics) are positioned a uniform distance from the pupil and are directed at an acute angle into the back of the person's eye. If the light delivery members are molded into a lens, the curvature of the lens must be considered when setting the angle of the light delivery member. With an ILF, which preferably includes visually transparent light delivery members on or in a lens, the fibers or wave guides that are directly over the pupil are preferably operated in a manner such that they will not transmit bright light to the eye. Hence, the direct input onto the cones, ganglia or other photoreceptors will be from the outside, and the circadian input would always be from the sides (off-normal axis based on forward gaze). This can be accomplished by tracking the pupil position, and providing light pulses from light delivery members that are off-normal axis from the detected position of the pupil.

Figure 2:
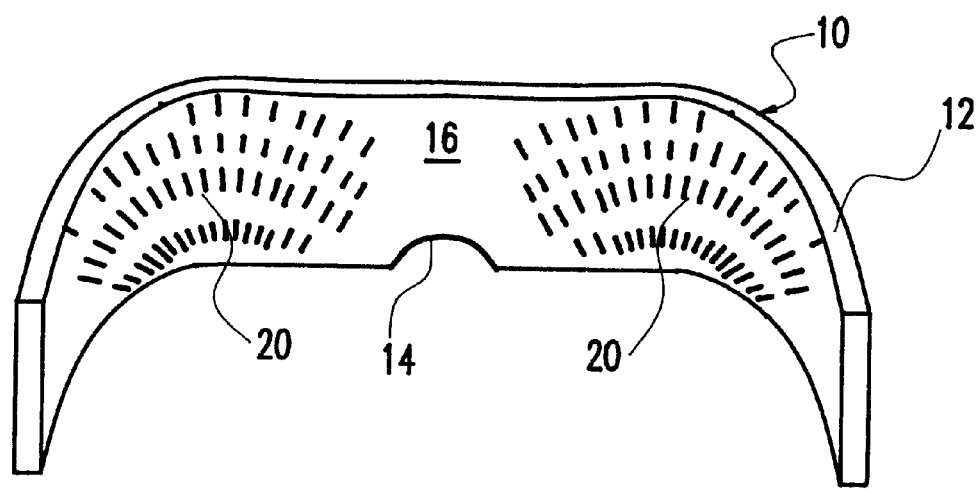
FIG. 2 is a rear perspective view as in FIG. 1, showing a fiber end array.

Referring now to FIGS. 1 and 2, in the preferred ILF embodiment, the present invention is housed in the form of eye-glasses or goggles, or clip-on lenses generally referred to by the reference numeral 10. The housing has a frame 12 defining the shape of the goggles 10 and include a nose piece 14. The lens(es) 16 can be constructed with an optical fiber matrix 18 in an eyeglass grade transparent material, such as plastic, to maximize visual acuity. Alternatively, a series of optical waveguides can be formed in or on the lens 16 using standard lithography, deposition or etching techniques, and will perform the same function as the optical fiber matrix 18 discussed below.

The fiber matrix pattern 18 and curvature of the lens 16 should be chosen to yield the highest visual acuity. Preferably, the fibers 18 or wave guides will be approximately index matched to the lens 16 material, such that they will essentially be transparent to the wearer. However, exact matching would not be preferred since so doing would lead to loss of light transmission.

In operation, light from LEDs or other light sources, preferably having a wavelength ranging from 500 nm to 560 nm, is launched into one end 22 of the optic fibers or wave guides at a power sufficient to yield an average back of the eye intensity of 12 to 2000 $\mu W/cm^2$. As shown in FIG. 2, the individual fibers 20 (or waveguides) in the array 18 preferably have an angled slice of preferably be approximately 45° on the end of the fiber so as to direct light into the pupil. Partial mirroring or end modification techniques can be used in producing the sliced fiber ends. In the case of an optical wave guide, prism like structures or mirrors/reflectors can be fabricated at the end of the wave guide to extract light into the eye.

Figure 3:
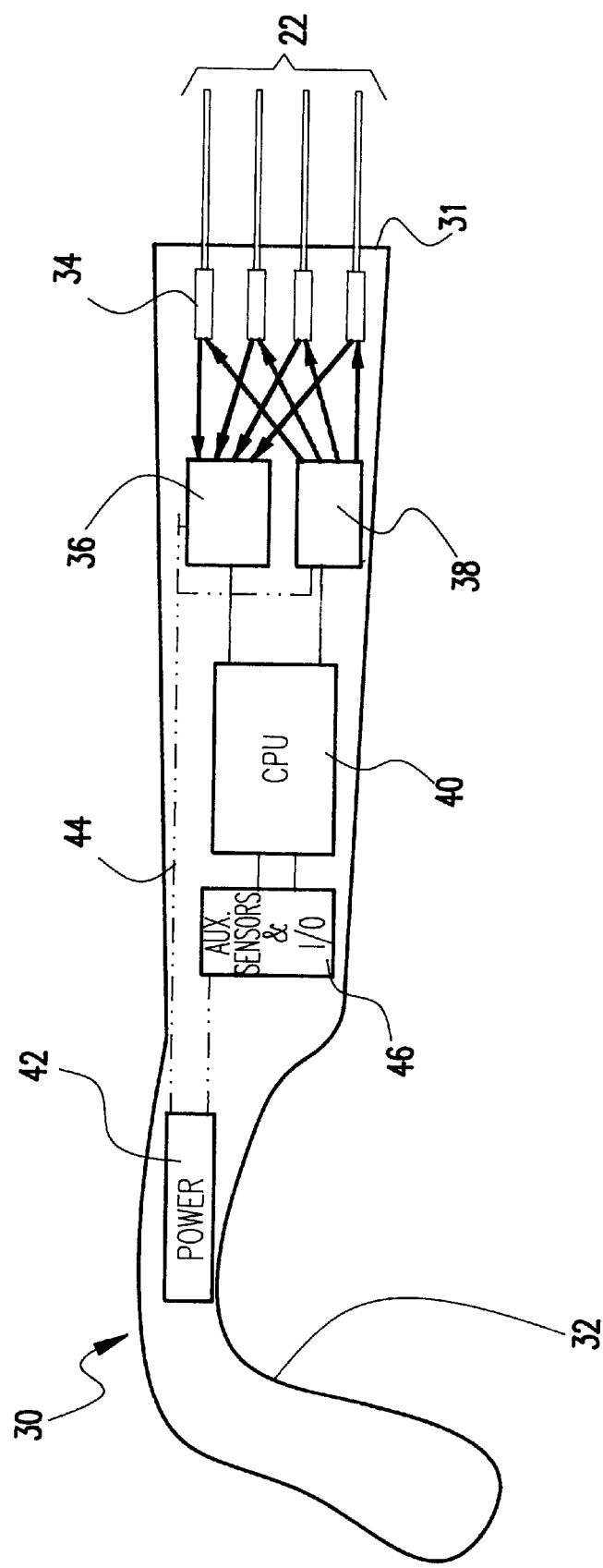
FIG. 3 is a side view of the side piece that connects to the front piece of FIG. 1.

Referring now to FIG. 3 there is shown an arm or side piece connected to the goggles or glasses front piece 10 shown in FIGS. 1 and 2. All of the electronics necessary to operate the ILF device preferably fit in the arm as shown in FIG. 3. The arm is designed to connect directly to the front piece 12 at end 31. An ear hook 32 is provided at an opposite end to secure the device to the wearer's head. Only one arm 30 is shown for simplicity. However, it is understood that in practice a pair of arms are employed by the device, one for each side of the user's head. In the preferred embodiment, each arm 30 is a mirror image of the other. However, all of the electronics necessary for both of the wearer's eyes may be housed in only one of the arms 32.

The fiber optic bundle 22 is input into individual couplers 34. Photo sensors 36 detect light delivered from individual fibers in the bundle 22. Alternatively, a charge coupled device, preferably of low resolution and rapid cycle speed, could be used in place of photo sensors 36. Light sources 38, such as, for example LEDs, are used to launch light into the individual fibers in the bundle 22. The present invention includes the ability to use various spectral LED components as well as the means of attaching a white light source to the fibers 22. The photo sensors 36 and the light sources 38 are controlled by a programmable central processing unit 40. A power supply 42, such as a battery, is connected with supply lines to the various components via power lines 44. The power supply 42 may be either internal or external. An auxiliary sensor and input/output unit 46 is provided to the CPU 40.

While FIG. 3 shows all the light emitting, receiving and controlling components in the arm 30 of a pair of goggles, it should be understood that in some applications, all of the components for light emitting, receiving and controlling can be housed in a portable, Walkman® type device together with a fiber optic bundle for delivering and receiving light from the lens 16. This arrangement would be particularly useful where it is important to position the circuitry such that electromagnetic (EM) fields or current is to stay off the wearer's head.

For tracking the pupil, the required timing response is in the MHz range. The LED's 38 should have fast duty cycles in case frequency must be increased. This is not a problem since nanosecond devices are common today. For tracking of the pupil, a 100 $\mu$sec on and 100 $\mu$sec off pulse cycle would be preferable to use. This is based on the maximum (frequent eye movement (FEM) or saccade) velocity of the pupil scanning the matrix of fibers, with a minimum of 10 sample time points between fiber crossings. This is a conservative position. Hence, fine timing adjustments should be made for comfort and effectiveness. To minimize interference with vision, the central fibers are blocked and the on-time frequency may have to be increased or otherwise adjusted for the individual. Vision interference may also be mitigated by back masking to delay response time effects which will tend to keep the image uniform across the field.

The CPU 40 is used to identify the position of the pupil with respect to the location of the ends of the fibers 20 or waveguides in the matrix. A fiber-end lensing technique can be used to allow efficient transmission and reception of the locator optical signals so that the ILF embodiment of the present invention will have the ability to work with visible spectra as well as infrared. Preferably, the arm 30 will have sufficient shielding to protect the user against long term FM exposure around the brain. The circuits have safety designs in them to protect against spurious high intensity bursts. This could be done, for example, by limiting the current to the LEDs 38 using the photo sensor readings 36 and a predetermined cutoff. The couplers 34 split light from optical source 38 into multiple fibers, as well as single LEDs to a limited number of fibers in the bundle 22. The CPU 40 processes the imaging data of the pupil and controls its tracking, specifically optimizing the system with respect to energy consumption, size, and weight. Detection speeds are fast enough such that the eye would not recognize any flicker.

In the preferred embodiment, the fibers 22 or waveguides are used in a dual mode to both deliver light to the back of the eye as well as sense light reflected back into the fiber from the eye and the outside scene. An optical splitter, such as a fiber optic coupler, may be used to shunt some of this returned light to a photo detector 36 or CCD where a reflected value would be obtained. The reflected light will be a function of where on the eye the reflection takes place. A map of all the reflection values from all the fibers 20 or wave guides will then show the exact position of the eye pupil as well as iris size and opening, and the degree to which the eyelid is closed. When fibers 20 are used, they will likely be plastic, being used in a ribbon arrangement. The ribbon arrangement allows practical coupling of another ribbon which results in all the coupler being made at once. In this case, the photo sensor 36 would comprise photo detector arrays or a CCD which matches the geometrical core to core spacing in the ribbon. Likewise an emitting diode array 38 would be used to directly couple the fiber ribbon to the LEDs. In an alternate embodiment, every other fiber is used as a source (coupled to the LED array 38) and the remaining fibers are coupled to a photo diode arrays 36.

Since each photo diode sensor 36 is addressable and each LED in the source array 38 is controllable, the CPU 40 can be used to find the centroid of the pupil and track its motion. Other parameters which the CPU 40 will measure are the degree of eye lid closing and the diameter of the pupil. In addition, the CPU 40 is able to shut-off the system for central optical fibers over the pupil, consistent with trying to maintain a high level of visual acuity. The control of each LED in the source array 38 allows virtually any pattern of illumination to be realized. There will be various geometries of illumination, such that the most beneficial patterns for the specific application can be applied. The system should be able to function with "on-cycles" on the order of microseconds to tens of microseconds, followed by "off-cycles" on the order of milliseconds. Timing will preferably be adjustable.

A temperature tracking sensor unit may be provided in the auxiliary unit 46 which comprises an infrared tympanic temperature measuring device. These are readily available and have good correlation with core body temperature as measured with blood flow in the heart region. A second temperature tracking module could use an appropriately mounted heat flux sensor. The auxiliary sensor and input/output unit 46 can therefore measure the temperature in the eye, corneal refractive changes, pupil changes and reactions, as well as pigment migration at the rear of the eye. The ILF embodiment of the present invention can incorporate the temperature cycle effectively into the operation, by tracking the time derivative of temperature with an appropriate numerical noise filter so that a real time response of the lighting cycle is obtained to correctly match up with the temperature cycle.

White light noise subtraction from the surrounding environment unit will enhance the practical application of the unit. A shut-off mechanism will be incorporated for circadian phase shifting if the device would be used in day light conditions of sufficient light intensity to generate a phase shift. The ILF embodiment of the present invention will have a few of its optical fibers 20 sampling the external light environment and connected to a radiometer. This will require the integration of either a single photo optically filtered photo diode sensor 36 or perhaps a small array of spectrally filtered photo diodes so that a profile of the ambient lighting conditions may be known. Once appropriate thresholds are reached, the photo diode signals would be sufficient to turn off the light sources 38. Further, during the user's dark cycle a warning would be sent, and continue to be sent, if the external illumination was too bright.

An important factor to consider in the practice of this invention is to keep the pupil dilated to maximize the coverage area. Very short light pulses with sufficient off-time can be used such that the eye and brain are tricked into retaining the night time or low light images rather than the general illumination of the region. There are indications from animal experiments that total dose is as important as dose rate. Accordingly, the aim is to get a sufficiently large number of photon spread around the back of the eye in the region where there are cones, but to limit the pulse length such that the visual track is not correctly stimulated. If the rods have sufficient time to freeze the outside image, this technique will work. As a modification, alternate regions of illumination and pulse width could be used to improve visual acuity.

Phase delays between right and left eyes will also be utilized to investigate improved visual acuity. Another option is to use reactive optics to more accurately control the light pattern and angle of entry. A technique of tracking pupil contraction as a means of self-regulating the intensity and spatial pattern in order to maximize night vision acuity may be used.

The auxiliary unit 46 is preferably also an input/output (I/O) unit. It will have the capability of feeding alpha-numeric information to an LED display on the outside of the side unit (not shown), and taking input from micro switches adjacent to that unit. There will also preferably be an audio output to an ear piece coming from the side of the unit. This ear piece unit could contain the infra-red detector fibers for the tympanic temperature unit. The audio output would be used as part of the warning and command system for the user such as to sound an awakening alarm if the user is about to fall asleep. The third I/O function would be a link connector to an external PC. The power pack 40 will either be an internal unit on each side, or a single external unit that could fit into a pocket. The unit will contain rechargeable batteries that can easily be replaced.

Figure 4:
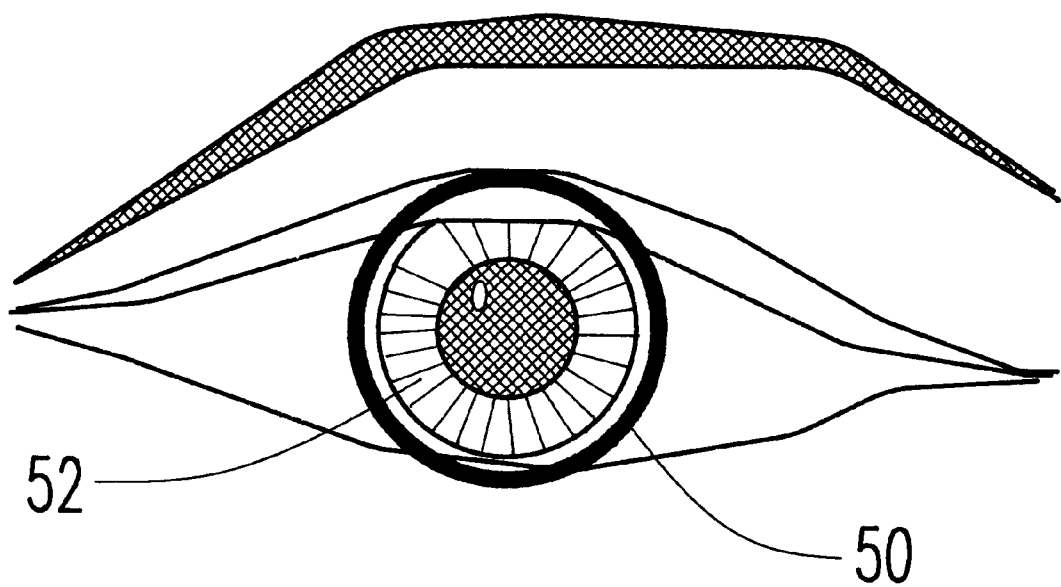
FIG. 4 is a plan view show ring shaped illumination elements positioned in front of a wearer's eyes.

FIG. 4 shows a static light field embodiment of this invention wherein a ring shaped light illumination element 50 is positioned in front of a wearer's eye. The illumination element 50 preferably has fiber optics 52 or waveguides positioned 360° about its periphery which are directed at an acute angle into the patient's eye (i.e., at the pupil). The circular-like matrix pattern of fiber ends or bundles of thin fiber ends 52 will have an inner diameter of 1–3 cm and in most cases approximately 2 cm. The ring shaped illumination element 50 can be positioned in or on eyeglasses or goggles, be part of a clip-on member which clips onto eyeglasses or goggles, or be a free standing element which can either have or not have a lens element. Photon stimulation provided by uniform off-fovia retinal illumination provides for enhanced alertness and other biological or psychological effects (e.g., melatonin suppression). In addition, the wearer's forward vision is unimpaired by the ring shaped illumination element 50 since the axis of the pupil extends through the center of the element 50 and is not obstructed by light carrying members. Uniform off-axis illumination will tend to cause the pupil to move towards a position aligned with the center of the ring shaped illumination elements in response to bright light emitted from the light delivery elements. This, in turn, will further assure uniform angular distribution of the illumination around the retina and off the fovea since the pupil will be centrally positioned. Variable spectra and intensity models for illumination can be applied to the light sources so as to permit the simulation of sunrise and sunset with a faithful representation of the associated spectrum at each point in this lighting cycle. Furthermore, the variable spectra and intensity control mode may be used for other applications such as for psychological or seratonergic stimuli and other photo neurological stimuli.

EXAMPLE 1

The present invention may be used as a convenient, inexpensive, interactive light delivery system to help mediate the detrimental effects of shift work. The unit will be programmable so that its use can be automated and contain slow eye movement monitoring and blinking rate monitoring for alertness. The design will accommodate any remote sensing device that can track the individual's circadian cycle. The ILF would also act as an alarm to warn an individual if he is in danger of falling asleep or being hypnotized.

EXAMPLE 2

A second application is directed to international jet travel. The ILF of the present invention will accommodate the associated software and hardware to be compatible with future airline multi-media units. This technology could be incorporated into virtual reality eye units to give the necessary photon stimulus for circadian shifting while the user is provided with entertainment. The concept could be similar to portable radio-type headphones, which can be plugged into the existing system. This would allow average consumers to take the ILFs with them, since in most cases it requires two days or more to accomplish a circadian phase shift to the new time zone. Similarly, the invention may be useful for the rapid deployment of alert troops in combat and other missions.

EXAMPLE 3

The present invention also has applications for sleep disorder sufferers, submarine crews and those affected by seasonal affected disorder (SAD). An added advantage is that the same device can be used as a tool for chronobiologists, working with humans, to conduct their research into the precise mechanisms and parameters (action spectrum) that lead to entrainment, phase shifting and stimulus, in an extremely cost effective manner. This device could also become an optometric tool giving real-time parameters while the eye is functioning normally.

While the invention has been described in terms of its preferred embodiments, those skilled in the art will recognize that the invention can be practiced with modification within the spirit and scope of the appended claims.

I claim:

1. A light field device, comprising:

a light source;

an array of optical fibers embedded in eye-wear, each optical fiber having a first end for receiving light input from said light source and a second end, said array of optical fibers being arranged with said second ends of said optical fibers spaced apart from one another; and means for projecting light output from said second ends of said optical fibers into an eye at an acute angle with respect to a pupil of said eye whereby the visual acuity of said eye is unimpaired.

2. A light field device, comprising:

a transparent lens;

a matrix of light carrying devices associated with said transparent lens, said matrix of light carrying devices being essentially transparent to an eye;

a light source for generating light to be delivered to said eye by said light carrying devices;

means for coupling said light carrying devices to said light source; and means for projecting light from at least a portion of said light carrying devices into said eye at an acute angle with respect to a pupil of said eye whereby the visual accuity of said eye is unimpaired.

3. A method for subjecting a human eye to a light field, comprising the steps of:

positioning an array of optical fibers in front of a patient's eye, said array being comprised of a circular-like matrix with an inner diameter ranging from 1 cm to 3 cm, each optical fiber having a first end for receiving light input from a light source and a second end, said array of optical fibers being arranged with said second ends of said optical fibers spaced apart from one another; and projecting light output from said second ends of said optical fibers into an eye at an acute angle off axis from a pupil of said eye so as to render visual acuity of said eye unimpaired.

4. Eyewear with light stimulation, comprising:

a light source;

a circular-like array of optical fibers with an inner diameter ranging from 1 cm to 3 cm, each optical fiber having a first end for receiving light input from said light source and a second end; and means for projecting light output from said second ends of said optical fibers into an eye at an acute angle with respect to a pupil of said eye whereby the visual acuity of said eye is unimpaired.

5. Eyewear as recited in claim 4 wherein said inner diameter is approximately 2 cm.

* * * * *